(12) United States Patent
Moszner et al.

(10) Patent No.: US 11,135,136 B2
(45) Date of Patent: Oct. 5, 2021

(54) DENTAL MATERIALS BASED ON URETHANE-GROUP-CONTAINING VINYLCYCLOPROPANE DERIVATIVES

(71) Applicant: Ivoclar Vivadent AG, Schaan (LI)

(72) Inventors: Norbert Moszner, Triesen (LI); Yohann Catel, Rans (CH); Urs Karl Fischer, Arbon (CH); Sven Tauscher, Knonau (CH)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 16/322,827

(22) PCT Filed: Aug. 1, 2017

(86) PCT No.: PCT/EP2017/069387
§ 371 (c)(1),
(2) Date: Feb. 1, 2019

(87) PCT Pub. No.: WO2018/024706
PCT Pub. Date: Feb. 8, 2018

(65) Prior Publication Data
US 2019/0167533 A1 Jun. 6, 2019

(30) Foreign Application Priority Data
Aug. 3, 2016 (EP) .................... 16182622

(51) Int. Cl.
*A61K 6/083* (2006.01)
*C08F 22/14* (2006.01)
(Continued)

(52) U.S. Cl.
CPC .............. *A61K 6/887* (2020.01); *C08F 22/14* (2013.01); *C08L 35/02* (2013.01); *C08L 2203/02* (2013.01)

(58) Field of Classification Search
CPC ..... A61K 6/083; C08L 35/02; C08L 2203/02; C08F 22/14
See application file for complete search history.

(56) References Cited

U.S. PATENT DOCUMENTS 4,713,478 A 12/1987 Fayter, Jr.
4,713,479 A 12/1987 Clark, Jr. et al.
(Continued)

FOREIGN PATENT DOCUMENTS

CA 2232915 A1 9/1998
DE 19714320 A1 10/1998
(Continued)

OTHER PUBLICATIONS

Database WPI, Week 201080 Thomson Scientific, London, GB; AN 2010-P22097 & JP 2010 260945 A.
(Continued)

*Primary Examiner* — Jessica M Roswell
(74) *Attorney, Agent, or Firm* — Ann M. Knab; Thad McMurray (57) ABSTRACT

Vinylcyclopropane of general formulae I in which X, Y in each case are O or NH, wherein X and Y cannot have the same meaning, $R^1$ is a linear or branched $C_1$-$C_8$-alkyl radical, which can be interrupted by O, S, an
(Continued)

ester group or a urethane group, $R^2$ is a linear or branched $C_2$-$C_{10}$-alkylene radical, which can be interrupted by O, S, an ester group or a urethane group, $R^3$ is a hydrocarbon radical with 1 to 20 carbon atoms, which additionally can contain one or more N, O or S atoms, and n is 1, 2, 3 or 4, preferably 1 or 2. The vinylcyclopropanes are characterized by a low shrinkage and a high reactivity on radical polymerization and are suitable in particular for the preparation of dental materials.

15 Claims, 1 Drawing Sheet

(51) Int. Cl.
    *C08L 35/02*     (2006.01)
    *A61K 6/887*     (2020.01)

(56) References Cited

U.S. PATENT DOCUMENTS

| | | | |
|---|---|---|---|
| 5,886,212 A | 3/1999 | Rheinberger et al. | |
| 6,034,151 A * | 3/2000 | Moszner | A61K 6/093 523/109 |
| 6,136,887 A * | 10/2000 | Moszner | A61K 6/0023 260/998.11 |
| 7,585,901 B2 | 9/2009 | Moszner et al. | |
| 7,595,354 B2 * | 9/2009 | Moszner | C08L 33/00 433/228.1 |
| 7,816,476 B2 | 10/2010 | Moszner et al. | |
| 8,466,212 B2 * | 6/2013 | Moszner | A61K 6/0017 106/35 |
| 8,921,450 B2 * | 12/2014 | Moszner | A61K 6/0023 106/35 |
| 2004/0077882 A1 * | 4/2004 | Moszner | A61K 6/887 549/23 |
| 2006/0178469 A1 * | 8/2006 | Moszner | A61K 6/30 524/556 |
| 2012/0010322 A1 | 1/2012 | Moszner et al. | |
| 2017/0022302 A1 * | 1/2017 | Kitadume | C08G 61/06 |
| 2018/0036209 A1 * | 2/2018 | Moszner | A61K 6/62 |

FOREIGN PATENT DOCUMENTS

| | | | |
|---|---|---|---|
| DE | 19812888 A1 | 10/1999 | |
| EP | 0867444 A2 | 9/1998 | |
| EP | 1413569 A1 | 4/2004 | |
| EP | 1686125 A1 | 8/2006 | |
| JP | 2010260945 A | 11/2010 | |

OTHER PUBLICATIONS

International Preliminary Report on Patentabilityof PCT/EP2017/069387, dated Feb. 5, 2019, 8 pages.
Viohl, J. et al., "The Chemistry of Dental Filling Plastics," Carl Hanser Verlag, Munich, Vienna, pp. 21-27, 1986.
Peutzfeldt, A., "Resin composites in dentistry: the monomer systems," European Journal of Oral Sciences, 105, pp. 97-116, 1997.
Nicholson, J.W. et al., "The Chemistry of Modern Dental Filling Materials," Journal of Chemical Education, vol. 76, No. 11, pp. 1497-1501, Nov. 1999.
Stansbury, J.W., "Curing Dental Resins and Composites by Photopolymerization," Journ. Esthet. Dent., 12, pp. 300-308, 2000.
Moszner, N. et al., "New Polymer-Chemical Developments in Clinical Dental Polymer Materials: Enamel-Dentin Adhesives and Restorative Composites," Journal of Polymer Science, Part A: Polymer Chemistry, 50, pp. 4369-4402, 2012.
Sadhir, R. K., et al., "Expanding Monomers, Synthesis, Characterization and Applications," CRC Press, Boca Raton, Ann Arbor, London, Tokyo, 1992.
Moszner, N. et al., "Synthesis and polymerization of vinylcyclopropanes," Macromol. Chem. Phys., 200, 2173-2187, 1999.
Sanda, F. et al., "Synthesis and Radical Ring-Opening Polymerization of a Vinylcyclopropane Bearing a Cyclic Carbonate Moiety, 1-Vinyl-5,7-dioxaspiro[2.5]octan-6-1," Macromolecules, 27, pp. 3986-3991, 1994.
Okazaki, T. et al., "Synthesis and Radical Ring-Opening Polymerization Behavior of Bifunctional Vinylcyclopropane Bearing a Spiroacetal Moiety," Macromolecules, 28, pp. 6026-6028, 1995.
Thomson, "XP-002766140," Nissan Chem. Ind. Ltd., 2004.
Moszner, N. et al., "Polymerization of Cyclic Monomers. VII. Synthesis and Radical Polymerization of 1,3-Bis[(1-alkoxycarbonyl-2-vinylcyclopropane-1-yl) carboxy]benzenes," Journal of Applied Polymer Science, vol. 72, pp. 1775-1782, 1999. John Wiley & Sons, Inc.
Moszner, N. et al., "Polymerization of cyclic monomers, 4a): Synthesis and radical polymerization of bi- and trifunctional 2-vinylcyclopropanes," Macromol. Rapid Comm., 18, pp. 775-780, 1997.
Moszner, N. et al., "Polymerization of Cyclic Monomers, 10a,b, Synthesis and Radical Polymerization of Methyl 2-(Bicyclo[3.1.0]hex-1-yl)acrylate," Macromol. Rapid Comm. 24, pp. 269-273, 2003.
Sanda, F. et al., "Radical Copolymerization of 1,1-Bis(ethoxycarbonyl)-2-vinylcyclopropane and Methyl Mathacrylate Accompanying Ring Opening and Cyclization," Macromolecules, 27, pp. 3982-3985, 1994.

* cited by examiner

DENTAL MATERIALS BASED ON URETHANE-GROUP-CONTAINING VINYLCYCLOPROPANE DERIVATIVES

CROSS-REFERENCE TO RELATED APPLICATIONS

This application is a National Stage application of International patent application PCT/EP2017/069387 filed on Aug. 1, 2017, which claims priority to European patent application No. 16182622.7 filed on Aug. 3, 2016, the disclosures of which are incorporated herein by reference in their entirety.

TECHNICAL FIELD

The present invention relates to urethane-group-containing vinylcyclopropanes which have a high reactivity on radical polymerization and which are suitable in particular for the preparation of dental materials, in particular of cements, composites, coating materials, bondings and adhesives. In addition, the vinylcyclopropanes a re suitable for the stereolithographic production of shaped bodies.

BACKGROUND OF THE INVENTION

The polymerizable organic matrix of dental resins, cements or composites consists above all of a mixture of monomers, initiator components, stabilizers and pigments (J. Viohl, K. Dermann, D. Quast, S. Venz, Die Chemie zahnärztlicher Füllungskunststoffe [The chemistry of dental filling plastics], Carl Hanser Verlag, Munich-Vienna 1986, 21-27). As resins, mixtures of dimethacrylates are usually used (cf. A. Peutzfeldt, Resin composites in dentistry: the monomer systems, Eur. J. Oral. Sci. 105 (1997) 97-116; J. W. Nicolson, H. M. Anstice, The chemistry of modern dental filling materials, J. Chem Ed. 76 (1999) 1497-1501; J. W. Stansburry, Curing dental resins and composites by photopolymerization, J. Esthet. Dent., 12 (2000) 300-308; N. Moszner, T. Hirt, New Polymer-Chemical Developments in Clinical Dental Polymer Materials: Enamel-Dentin Adhesives and Restorative Composites, J. Polym. Sci. Part A: Polym. Chem. 50 (2012) 4369-4402).

A main disadvantage of the methacrylates used is that the polymerization thereof is accompanied by a volume contraction, so-called polymerization shrinkage. In the case of dental materials, polymerization shrinkage can lead, among other things, to disadvantageous shrinkage stresses and to marginal gap formation in filling composites, to reduced substrate adhesion in fixing composites or coating materials and to the dimensional stability of prosthesis plastics being impaired. In this connection, radically polymerizable cyclic monomers have attracted great interest in the preparation of dental materials due to the considerably lower polymerization shrinkage compared with linear monomers, such as e.g. methacrylates (cf. R. K. Sadhir, R. M. Luck, Expanding Monomers, CRC Press, Boca Raton etc. 1992).

Vinylcyclopropanes are characterized, compared with other known ring-opening monomers such as methylene-group-containing spiroorthocarbonates (SOC), spiroorthoesters (SOE) or bicyclic orthoesters (BOE), by the fact that the vinylcyclopropyl (VCP) group is not moisture-sensitive and in that, when it is radically polymerized, polymers with high molar masses are obtained which only contain hydrolytically stable C—C bonds in the main chain (N. Moszner, F. Zeuner, T. Völkel, V. Rheinberger, Macromol. Chem. Phys. 200 (1999) 2173).

From DE 198 12 888 A1, vinylcyclopropane derivatives and in particular vinylcyclopropane (meth)acrylates are known which can be copolymerized with acrylates and methacrylates.

Moreover, vinylcyclopropanes with several polymerizable groups are known. F. Sanda, T. Takata, T. Endo, Macromolecules 27 (1994) 3986, describe 1-vinyl-5,7-dioxaspiro[2.5]octan-6-one, a hybrid monomer which contains a vinylcyclopropane group and a cyclic carbonate group, and T. Okazaki, F. Sanda, T. Endo, Macromolecules 28 (1995) 6026, describe 1,10-bis(vinyl)-4,8,12,15-tetraoxa-trispiro-[2.2.2.2.2.2]pentadecane, a monomer in which two vinylcyclopropane groups are joined to each other via a hydrolysis-sensitive spiroacetal unit. These compounds do not have an improved radical copolymerizability with (meth)acrylic compounds in comparison with monofunctional vinylcyclopropanes.

EP 0 798 286 A1 relates to multifunctional vinylcyclopropane derivatives with two to six vinylcyclopropane groups which enable the preparation of crosslinked polymers.

Using the example of the radical copolymerization of 1,1-bis(ethoxycarbonyl)-2-vinylcyclopropane with methyl methacrylate (MMA), it could be shown (F. Sanda, T. Takata, T. Endo, Macromolecules, (1994) 3982) that, compared with methacrylates, vinylcyclopropanes are characterized by a lower radical polymerizability, which considerably restricts their practical use. It is particularly disadvantageous that the known 1,1-bis(alkoxycarbonyl)-2-vinylcyclopropanes which are easy to obtain have a low photopolymerization activity.

EP 1 413 569 A1 discloses dental materials based on bicyclic cyclopropane derivatives such as e.g. 2-[bicyclo[3.1.0]hex-1-yl]acrylic acid methyl ester, which exhibit an improved reactivity on radical polymerization (N. Moszner, F. Zeuner, U. K. Fischer, V. Rheinberger, A. de Meijere, V. Bagutski, Macromol. Rapid. Commun. 24 (2003) 269). However, these more reactive monofunctional bicyclic cyclopropyl acrylates can only be obtained with great difficulty.

SUMMARY OF THE INVENTION

The object of the invention is to provide radically polymerizable monomers which shrink only slightly on radical polymerization and which have a high radical polymerization reactivity, in particular on photopolymerization. In addition, the monomers are to be easily obtainable through synthesis and suitable for the preparation of dental materials such as adhesives, cements or composites and for the production of coatings and shaped bodies, for example for the stereolithographic production of shaped bodies.

BRIEF DESCRIPTION OF THE DRAWINGS

Further advantages, details and features may be taken from the following description of exemplary embodiments of the invention in conjunction with the drawings.

DETAILED DESCRIPTION

This object is achieved by urethane-group-containing vinylcyclopropanes corresponding to general formulae I:

in which

X, Y in each case are O or NH, wherein X and Y cannot have the same meaning, $R^1$ is a linear or branched $C_1$-$C_8$-alkyl radical, which can be interrupted by O, S, an ester group and/or a urethane group, $R^2$ is a linear or branched $C_2$-$C_{10}$-alkylene radical, which can be interrupted by O, S, an ester group and/or a urethane group, $R^3$ is a hydrocarbon radical with 1 to 20 carbon atoms, which additionally can contain one or more N, O or S atoms, and n is 1, 2, 3 or 4, preferably 1 or 2.

The urethane group optionally present in $R^1/R^2$ is preferably a non-N-substituted group of the formula —NH—CO—O—.

Formula I and the other formulae shown herein cover all stereoisomeric forms as well as mixtures of different stereoisomeric forms, such as e.g. racemates. The formulae only relate to those compounds which are compatible with the theory of chemical valence. The indication that a radical can be interrupted by a group or a heteroatom such as O is understood to mean that the group or the heteroatom is inserted into the carbon chain or the carbon ring of the radical, i.e. is bordered on both sides by carbon atoms. The number of heteroatoms or groups is therefore smaller by at least 1 than the number of carbon atoms, and the heteroatoms cannot be terminal. $C_1$ radicals cannot be interrupted. In the case of hydrocarbon radicals, which contain carbon atoms and heteroatoms, the number of heteroatoms is always smaller than the number of carbon atoms without taking into account substituents. The radicals $R^1$ and/or $R^2$ can be interrupted by one or more of the named atoms and groups. Radicals are preferred which are interrupted by one group or one atom or are particularly preferred which are not interrupted.

The vinylcyclopropanes according to the invention contain at least one urethane group, i.e. in formula I, X must have the meaning O if Y has the meaning NH, or X is NH if Y represents O. X and Y cannot have the same meaning.

The radical $R^3$ is substituted n times by the expression in brackets. $R^3$ is a hydrocarbon radical with 1 to 20 carbon atoms, which can contain one or more N, O or S atoms. Preferably $R^3$ is an aliphatic linear or branched $C_1$-$C_{20}$-hydrocarbon radical, which can be interrupted by O, S or an ester group, an alicyclic or aromatic $C_6$-$C_{14}$ radical or an aromatic or non-aromatic heterocyclic radical, which can contain 4 to 20 carbon atoms and 1 to 6 heteroatoms, which are selected from N, O and/or S atoms. The named cyclic radicals can be mono- or polycyclic groups. $R^3$ can also be formed by a combination of the named radicals, for example by a combination of one or more aliphatic and one or more aromatic groups, e.g. an aliphatic-aromatic $C_7$-$C_{20}$ radical. Particularly preferred are radicals which contain a tricyclodecane group (TCD).

The compounds of formula I are radically polymerizable. Compounds in which n is greater than 1 contain two or more vinylcyclopropane groups. Herein, such compounds are also referred to as multifunctional vinylcyclopropanes and compounds with only one vinylcyclopropane group are correspondingly referred to as monofunctional vinylcyclopropanes.

According to the invention, compounds of formula I are preferred in which the variables have the following meanings:

X, Y in each case O or NH, wherein X and Y cannot have the same meaning, $R^1$ a branched or preferably linear $C_1$-$C_4$-alkyl radical, $R^2$ a branched or preferably linear $C_2$-$C_4$-alkyl radical, $R^3$ an aliphatic linear or branched $C_1$-$C_{20}$-hydrocarbon radical, an aromatic $C_6$-$C_{14}$ radical, an aromatic or non-aromatic heterocyclic radical, which contains 4 to 12 carbon atoms and 1 to 2 heteroatoms, which are selected from N or O atoms, an alicyclic $C_6$-$C_{12}$-hydrocarbon radical, wherein in all cases the cyclic radicals can be mono- or polycyclic groups, or an aliphatic-aromatic $C_7$-$C_{20}$ radical, n 1 or 2.

According to the invention, compounds of formula I are particularly preferred in which the variables have the following meanings:

X, Y in each case O or NH, wherein X and Y cannot have the same meaning, $R^1$ a methyl or ethyl radical,

$R^2$ a linear $C_2$-$C_4$-alkylene radical, $R^3$ an aliphatic linear or branched $C_1$-$C_{10}$-hydrocarbon radical, an aromatic $C_6$-$C_{14}$ radical, an alicyclic $C_6$-$C_{12}$-hydrocarbon radical, wherein in all cases the cyclic radicals can be mono- or polycyclic groups, or an aliphatic-aromatic $C_7$-$C_{15}$ radical, n 1 or 2.

The vinylcyclopropanes of formula I are characterized by a low shrinkage and a high reactivity on radical polymerization. A subject of the present invention is also the use of urethane-group-containing vinylcyclopropanes of Formula I for the preparation of dental materials, in particular of dental cements, composites, coating materials, bondings and adhesives, as well as for the preparation of materials for the stereolithographic production of molded articles. A further subject of the invention are molded articles, polymers and copolymers which can be obtained by homo- or copolymerization of the urethane-group-containing vinylcyclopropanes of formula I.

The urethane-group-containing monofunctional or multifunctional vinylcyclopropanes of general formulae I can be prepared easily. The synthesis of 1,1-di(alkoxycarbonyl)-substituted 2-vinylcyclopropanes can take place using known methods (cf. U.S. Pat. Nos. 4,713,478 and 4,713,479) e.g. through reaction of trans-1,4-dihalogenbut-2-enes with corresponding malonic acid esters:

For example:

2-Vinylcyclopropane-1-alkoxycarbonyl-1-carboxylic acids can be prepared from the 1,1-di(alkoxycarbonyl)-substituted 2-vinylcyclopropanes by partial alkaline hydrolysis:

For example:

Corresponding hydroxyalkyl derivatives can be synthesized from the 2-vinylcyclopropane-1-alkoxycarbonyl-1-carboxylic acids through reaction with diols in the presence of dicyclohexylcarbodiimide (DCC) and 4-dimethylaminopyridine (DMAP):

For example:

The reaction between such hydroxyalkyl derivatives and mono- or multifunctional isocyanates results in the urethane-vinylcyclopropanes according to the invention:

-continued

For example:

Corresponding dihydroxyalkyl derivatives can be prepared from the 2-vinylcyclopropane-1,1-dicarboxylic acid through reaction with diols in the presence of DCC and DMAP. Such compounds could then react with isocyanates to form the corresponding diurethanes:

Corresponding Boc-protected amines can be synthesized from the 2-vinylcyclopropane-1-alkoxycarbonyl-1-carboxylic acids through reaction with N-Boc-hydroxyalkylamines (Boc=tert-butoxycarbonyl) in the presence of DCC and DMAP. De-protection with trifluoroacetic acid (TFA) yields the corresponding amines:

Specific example:

These amines can then be converted into urethane derivatives according to the invention through reaction with dialkyl carbonates.

For example:

With this method, multifunctional vinylcyclopropanes can be prepared in the following way:

A further possibility for the synthesis of the urethane-group-containing mono- or multifunctional vinylcyclopropanes of general formula I consists in the reaction of vinylcyclopropane amines with alkyl chloroformates. The alkyl chloroformates can be synthesized from the bis (trichloromethyl) carbonate and the corresponding alcohol:

Specific example:

Preferred examples of urethane-group-containing monofunctional or multifunctional vinylcyclopropanes of general formulae I according to the invention are:

The polymerizable urethane-group-containing vinylcyclopropanes of general formula I are mostly liquid and surprisingly exhibit a considerably improved radical polymerizability, in particular on photopolymerization, compared with 1,1-bis(alkoxycarbonyl)-2-vinylcyclopropanes, and a lower polymerization shrinkage compared with acyclic methacrylates. Dental materials such as fixing cements or filling composites with likewise reduced polymerization shrinkage can be prepared therewith.

The (dental) materials according to the invention preferably contain 2 to 95 wt.-%, particularly preferably 5 to 85 wt.-%, quite particularly preferably 5 to 60 wt.-% and in particular 10 to 60 wt.-% vinylcyclopropane(s) of general formula I, in each case relative to the total mass of the material.

In addition to one or more vinylcyclopropanes of general formula I, the materials preferably contain at least one further radically polymerizable monomer. As further radically polymerizable monomers, other vinylcyclopropanes such as 1,1-di(ethoxycarbonyl)- or 1,1-di(methoxycarbonyl)-2-vinylcyclopropane, bis(2-vinylcyclopropane-1-carboxylic acid ethyl ester-1-carbonamido)-2,2-dimethyl-4-methylhexane, 1,8-bis(2-vinylcyclopropane-1-carboxylic acid ethyl ester-1-carbonyloxy)-3,6-dioxaoctane (VCP 5) or the esters of 1-ethoxycarbonyl- or 1-methoxycarbonyl-2-vinylcyclopropane-carboxylic acid with ethylene glycol, 1,1,1-trimethylolpropane, 1,4-cyclohexanediol or resorcinol are preferred, such as bis-(2-vinyl-1,1-dicarboxylic acid monoethyl ester)resorcinyl ester (VCP 4), and in particular the 2-vinylcyclopropanes described in N. Moszner, F. Zeuner, V. Rheinberger, Macromol. Rapid Commun. 18 (1997) 775-780, and N. Moszner, F. Zeuner, T. Volkel, U. K. Fischer, V. Rheinberger, J. Appl. Polym. Sci. 72 (1999) 1775-1782. Further preferred are the bicyclic cyclopropane derivatives disclosed in EP 1 413 569 A1, in particular 2-(bicyclo[3.1.0]hex-1-yl)acrylic acid methyl or ethyl ester or the disubstitution products in 3-position thereof such as (3,3-bis(ethoxycarbonyl)bicyclo[3.1.0]hex-1-yl)acrylic acid methyl or ethyl ester.

Likewise preferred are the cyclopropyl acrylates disclosed in EP 688 125 A1, in particular {3,3-bis(ethoxycarbonyl)bicyclo[3.1.0]hexa-1-yl}acrylic acid methyl ester and 2-(3-acetyl-3-ethoxycarbonyl-bicyclo[3.1.0]hexa-1-yl}acrylic acid methyl ester.

According to the invention, those dental materials are preferred which contain as comonomer at least one monofunctional vinylcyclopropane with general formulae II:

II in which

A, B independently of each other in each case are OH or COOH,

X, Y independently of each other in each case are O or NH, $R^1$, $R^2$ independently of each other in each case are H or an aliphatic linear or branched $C_1$-$C_{10}$-hydrocarbon radical, which can be interrupted by O, S or an ester group, an alicyclic or aromatic $C_6$-$C_{14}$ radical or an aromatic or non-aromatic heterocyclic radical, which can contain 4 to 14 carbon atoms and 1 to 6 heteroatoms, which are selected from N, O and/or S atoms, and n, m independently of each other in each case are 0, 1 or 2.

If $X=Y=O$, $R^1 \neq H$ and $R^2 \neq H$, then $n+m \geq 1$. If $m=0$ and $R^1 \neq H$, the free valence at $R^1$ is filled by H, and if $n=0$ and $R^2 \neq H$, the free valence at $R^2$ is correspondingly filled by H.

The compounds of formula II are characterized by the fact that they have groups (CO—NH, OH, COOH) which are suitable for the formation of hydrogen bridge bonds. The vinylcyclopropanes of formula II have a low viscosity and are therefore particularly suitable as diluting monomers for viscous monomers.

Compounds of formula II in which A and B have the same meaning are preferred. Likewise, those compounds are preferred in which X and Y have the same meaning. $R^1$ and $R^2$ can be identical or, preferably, different. The radicals $R^1$ and/or $R^2$ of formula II can be interrupted by one or more of the named atoms and groups. Radicals are preferred which are interrupted by one group or one atom, and particularly preferred are radicals which are not interrupted.

The named cyclic radicals of Formula II can be mono- or polycyclic groups. $R^1$ and/or $R^2$ can also be formed by a combination of the named radicals, for example by a combination of one or more aliphatic and one or more aromatic groups, e.g. an aliphatic-aromatic $C_7$-$C_{14}$ radical. Particularly preferred are radicals which contain a tricyclodecane group (TCD).

According to the invention, compounds of Formula II are preferred in which the variables have the following meanings:

A OH, m 0, 1 or 2, $R^1$ H or a branched or preferably linear $C_1$-$C_6$-hydrocarbon radical, which can be interrupted by O, wherein radicals which are not interrupted by O are preferred, wherein $R^1$ is preferably not H if $X=O$ and $m=0$, X O or NH, wherein X is preferably NH if $m=0$ and $R^1 \neq H$, n 0, $R^2$ a branched or preferably linear $C_1$-$C_3$-alkyl radical,

Y O;

or preferably

B OH, n 0, 1 or 2, $R^2$ H or a branched or preferably linear $C_1$-$C_6$-hydrocarbon radical, which can be interrupted by O, wherein radicals which are not interrupted by O are preferred, wherein $R^2$ is preferably not H if $Y=O$ and $n=0$, Y O or NH, wherein Y is preferably NH if n=0 and $R^2 \neq H$,
m 0,
$R^1$ a branched or preferably linear $C_1$-$C_3$-alkyl radical,
X O.

Compounds of formula II are particularly preferred in which the variables have the following meanings:
A OH,
m 0 or 1,
$R^1$ H or a linear $C_1$-$C_6$-hydrocarbon radical, wherein $R^1$ is preferably not H if X=O and m=0,
X O or NH, wherein X is NH if m=0 and $R^1 \neq H$,
n 0,
$R^2$ a linear $C_1$-$C_3$-alkyl radical,
Y O;
or preferably
B OH,
n 0 or 1,
$R^2$ H or a linear $C_1$-$C_6$-hydrocarbon radical, wherein $R^2$ is preferably not H if Y=O and n=0,
Y O or NH, wherein Y is NH if n=0 and $R^2 \neq H$,
m 0,
$R^1$ a linear $C_1$-$C_3$-alkyl radical,
X O.

In addition, the dental materials can also contain radically polymerizable mono- or polyfunctional (meth)acrylic acid derivatives. By monofunctional monomers is meant compounds with one, by multifunctional monomers is meant compounds with two or more, preferably 2 to 4 radically polymerizable groups.

Preferred mono- or multifunctional methacrylates are methyl, ethyl, 2-hydroxyethyl, butyl, benzyl, tetrahydrofurfuryl or isobornyl (meth)acrylate, p-cumylphenoxyethylene glycol methacrylate (CMP-1E), bisphenol A di(meth)acrylate, bis-GMA (an addition product of methacrylic acid and bisphenol A diglycidyl ether), ethoxylated or propoxylated bisphenol A dimethacrylate, such as e.g. the bisphenol A dimethacrylate 2-[4-(3-methacryloyloxyethox-yethyl)phenyl]-2-[4-(3-methacryloyloxyethyl)phenyl]propane (SR-348c) with 3 ethoxy groups or 2,2-bis[4-(2-(meth)acryloxypropoxy)phenyl]propane, UDMA (an addition product of 2-hydroxyethyl methacrylate (HEMA) and 2,2,4-trimethylhexamethylene diisocyanate), TMX-UDMA (an addition product of a mixture of HEMA and hydroxypropyl methacrylate (HPMA) with α,α,α',α'-tetramethyl-m-xylylene diisocyanate (TMXDI)), di-, tri- or tetraethylene glycol di(meth)acrylate, trimethylolpropane tri(meth)acrylate, pentaerythritol tetra(meth)acrylate, as well as glycerol di- and tri-methacrylate, 1,4-butanediol di(meth)acrylate, 1,10-decanediol di(meth)acrylate ($D_3MA$) or 1,12-dodecanediol di(meth)acrylate.

Moreover, the dental materials can advantageously also contain radically polymerizable, acid-group-containing monomers, such as e.g. polymerizable carboxylic acids, phosphonic acids and phosphoric acid esters. Preferred examples of polymerizable carboxylic acid monomers are maleic acid, 2-(hydroxymethyl)acrylic acid and 4-(meth)acryloyloxyethyltrimellitic acid anhydride. Preferred examples of suitable phosphonic acid monomers are 2-methacryloyloxyethyl phosphonic acid, 2-methacrylamidoethyl phosphonic acid, 2-[4-(dihydroxyphosphoryl)-2-oxa-butyl]-acrylic acid ethyl or 2,4,6-trimethyl phenyl ester. Preferred examples of suitable acidic polymerizable phosphoric acid esters are 2-methacryloyloxypropyl dihydrogen phosphate, 2-methacryloyloxyethyl dihydrogen phosphate, 2-methacryloyloxyethylphenyl hydrogen phosphate, di-pentaerythritol-pentamethacryloyloxy phosphate, 10-methacryloyloxydecyl dihydrogen phosphate and 6-(methacrylamido)hexyl dihydrogen phosphate. Acidic monomers serve primarily to improve the adhesion of the materials to dentine and/or tooth enamel. The amount of acidic monomers preferably lies in the range of from 0 to 20 wt.-%, preferably 0 to 15 wt.-% and particularly preferably 0 to 10 wt.-%, relative to the total mass of the dental material.

Materials are particularly preferred which contain at least one multifunctional radical monomer, i.e. a vinylcyclopropane of formula I and/or another multifunctional radically polymerizable monomer.

The dental materials according to the invention preferably furthermore contain an initiator for the radical polymerization. To initiate the radical photopolymerization, benzophenone, benzoin and derivatives thereof or α-diketones or derivatives thereof such as 9,10-phenanthrenequinone, 1-phenyl-propane-1,2-dione, diacetyl or 4,4'-dichlorobenzil are preferred. Particularly preferably used are camphorquinone and 2,2-dimethoxy-2-phenyl-acetophenone and quite particularly preferably used are α-diketones in combination with amines as reducing agent, such as e.g. 4-(dimethylamino)benzoic acid ethyl ester, N,N-dimethylaminoethyl methacrylate, N,N-dimethyl-sym.-xylidine or triethanolamine. Particularly suitable are also Norrish type I photoinitiators, in particular acyl- or bisacylphosphine oxides, such as for example the commercially available compounds 2,4,6-trimethylbenzoyldiphenylphosphine oxide and bis(2,4,6-trimethylbenzoyl)phenylphosphine oxide. Particularly suitable are also monoacyl trialkyl, diacyl dialkyl germanium, triacyl alkyl as well as tetraacyl germanium compounds, such as e.g. benzoyl trimethyl germanium, dibenzoyl diethyl germanium or bis(4-methoxybenzoyl) diethyl germanium as well as tetrabenzoyl germanium. Mixtures of the different photoinitiators can also be used, such as e.g. dibenzoyl diethyl germanium in combination with camphorquinone and 4-dimethylaminobenzoic acid ethyl ester or tetrabenzoyl germanium. Advantageously, initiator combinations can also be used which additionally contain aromatic diaryliodonium or triarylsulfonium salts, for example the commercially available compounds 4-octyloxyphenyl-phenyl-iodonium hexafluoroantimonate or isopropylphenyl-methylphenyl-iodonium tetrakis (penta fluoro phenyl) borate.

As initiators for a polymerization carried out at room temperature, redox initiator combinations are preferably used, such as e.g. combinations of benzoyl peroxide with N,N-dimethyl-sym.-xylidine or N,N-dimethyl-p-toluidine. Moreover, redox systems consisting of peroxides or hydroperoxides and reducing agents, such as e.g. ascorbic acid, barbiturates, thioureas or sulfinic acids, are also particularly suitable. In addition, compounds of transition metals which exhibit at least two stable valence states can be used as redox catalysts. These are preferably compounds of the elements copper, iron, vanadium, nickel or cobalt, wherein copper compounds are particularly preferred and these are preferably used as compounds with good organosolubility, such as e.g. as acetylacetonate, naphthenate or 2-ethylhexanoate.

Dental materials which contain at least one photoinitiator are preferred according to the invention. The materials can additionally contain further initiators.

Furthermore, the compositions used according to the invention preferably also contain at least one organic or particularly preferably inorganic particulate filler, for example to improve the mechanical properties or to set the viscosity. Preferred inorganic particulate fillers are amorphous spherical materials based on oxides, such as $SiO_2$, $ZrO_2$ and $TiO_2$ or mixed oxides of $SiO_2$, $ZrO_2$ and/or $TiO_2$, nanoparticulate or microfine fillers, such as pyrogenic silica or precipitated silica (weight-average particle size of 10-1000 nm), as well as minifillers, such as quartz, glass ceramic or glass powder with a weight-average particle size of from 0.01 to 1 µm. Further preferred fillers are X-ray opaque fillers, such as ytterbium trifluoride, nanoparticulate tantalum(V) oxide, barium sulfate, mixed oxides of $SiO_2$ with ytterbium(III) oxide or tantalum(V) oxide (weight-average particle size of from 10-1000 nm) and X-ray opaque glass powder, e.g. barium or strontium aluminium silicate glasses (weight-average particle size of from 0.2-10 µm).

To improve the bond between the filler particles and the cross-linked polymerization matrix, the filler particles can be surface-modified with suitable coupling reagents. For $SiO_2$-based fillers such as $SiO_2$, quartz, glass ceramic or glass powder, trialkoxysilanes, such as e.g. 3-methacryloyloxypropyltrimethoxysilane, are particularly suitable. Preferred are trialkoxysilanes which contain vinylcyclopropane groups, more preferably the vinylcyclopropane silanes described in EP 0 867 444 A2, in particular 1-methoxy- or 1-ethoxycarbonyl-1-[(3-trimethoxy- or 3-triethoxysilyl)propylaminocarbonyl)]-2-vinylcyclopropanes. Specifically, vinylcyclopropane silanes with the following structures are particularly suitable:

For the surface modification of non-silicate fillers, e.g. of $ZrO_2$ or $TiO_2$, functionalized acidic phosphates, such as e.g. 10-methacryloyloxy dihydrogen phosphate can also be used.

Optionally, the compositions used according to the invention can contain one or more further additives, above all solvents, preferably water, ethanol or a mixture thereof, as well as stabilizers, such as e.g. polymerization stabilizers, flavouring agents, dyes, microbiocidal active ingredients, fluoride-ion-releasing additives, optical brighteners, plasticizers and/or UV absorbers.

The materials according to the invention are suitable in particular as dental cements, filling materials, coating or veneering materials.

According to the invention, those dental materials are preferred which contain the following components:

a) 2 to 95 wt.-%, preferably 2 to 90 wt.-% and particularly preferably 10 to 85 wt.-% of at least one vinylcyclopropane of general formula I, b) 0.01 to 5 wt.-%, preferably 0.1 to 3.0 wt.-%, particularly preferably 0.2 to 2 wt.-% of at least one initiator for the radical polymerization, preferably a photoinitiator, c) 0 to 80 wt.-%, preferably 0 to 60 wt.-% and particularly preferably 0 to 50 wt.-% of other monomer(s), and optionally d) 0 to 85 wt.-%, preferably 0 to 80 wt.-% filler(s).

The filler content is determined decisively by the desired application of the dental material. Dental materials for use as coating material particularly preferably contain 0 to 40 wt.-%, dental materials for use as cement preferably 10-70 wt.-% and dental materials for use as filling material (filling composite) preferably 10-85 wt.-% filler(s).

Dental materials for use as filling material quite particularly preferably have the following composition:

a) 2 to 60 wt.-%, preferably 5 to 60 wt.-% and particularly preferably 10 to 60 wt.-% of at least one vinylcyclopropane of general formula I, b) 0.1 to 3 wt.-%, preferably 0.2 to 3.0 wt.-%, particularly preferably 0.2 to 1 wt.-% of at least one initiator for the radical polymerization, preferably a photoinitiator, c) 0 to 50 wt.-%, preferably 0 to 40 wt.-% and particularly preferably 0 to 30 wt.-% of other monomer(s), and d) 10 to 85 wt.-%, preferably 10 to 80 wt.-% filler(s).

Unless otherwise stated, all quantities herein relate to the total mass of the material. The individual quantity ranges can be chosen separately.

Those materials are particularly preferred which consist of the named components. Furthermore, those materials are preferred in which the individual components in each case are selected from the above-named preferred and particularly preferred substances.

According to the invention, those dental materials are particularly preferred which contain exclusively monomers which have vinylcyclopropyl (VCP) groups as radically polymerizable groups.

The materials according to the invention are suitable in particular as dental materials, in particular as dental adhesives, cements, filling composites and veneering materials as well as as materials for the production of prostheses, artificial teeth, inlays, onlays, crowns and bridges. They are characterized compared with materials based on dimethacrylates by a considerably lower polymerization shrinkage and compared with known polymerizable cyclopropane derivatives by a better polymerization reactivity, in particular on photopolymerization.

The dental materials are suitable primarily for intraoral application by the dentist for the restoration of damaged teeth (clinical materials), e.g. as dental cements, filling composites and veneering materials. However, they can also be used extraorally, for example in the production or repair of dental restorations, such as prostheses, artificial teeth, inlays, onlays, crowns and bridges (technical materials). The materials are suitable in particular for the production of molded articles, for example of dental restorations, by generative processes, in particular by stereolithography or 3D printing (cf. A. Gebhardt, Generative Fertigungsverfahren [Generative manufacturing processes], 3rd ed., Carl Hanser Verlag, Munich 2007).

The invention is explained in more detail in the following with reference to embodiment examples.

EXAMPLES

Example 1

Synthesis of 1-(2-ethylcarbamoyloxyethoxycarbonyl)-1-ethoxy-carbonyl-2-vinylcyclopropane (VCP-1)

Step 1: Synthesis of 1-(2-hydroxyethoxycarbonyl)-1-ethoxy-carbonyl-2-vinylcyclopropane (VCP-OH)

To a stirred solution of 1-ethoxycarbonyl-2-vinylcyclopropane-carboxylic acid (36.8 g, 200 mmol), ethylene glycol (49.7 g, 800 mmol) and 4-dimethylaminopyridine (DMAP, 1.22 g, 1.0 mmol) in anhydrous methylene chloride (30.0 ml), dicyclohexylcarbodiimide (DCC, 41.2 g, 200 mmol) was added portionwise under argon and at 0° C. Stirring continued for 30 min at 0° C. and 15 h at RT. The reaction mixture was suctioned over a frit and the residue was washed with methylene chloride (3×40 ml). The organic phase was washed with water (150 ml) and the aqueous phase was extracted with DCM (2×30 ml). The combined organic phases were dried over anhydrous sodium sulfate. The solvent was distilled off under vacuum and the crude product was purified by chromatography (flash silica gel with ethyl acetate/hexane: 1/3). 32.44 g (71% yield) of a colourless liquid was obtained as a mixture of diastereoisomers (ratio: approx. 9/1).

NMR analysis of the main isomer: $^{1}$H NMR (400 MHz, CDCl$_3$): δ=1.27 (t, $^{3}J_{HH}$=7.1 Hz, 3H, OCH$_2$CH$_3$); 1.60; (dd, $^{2}J_{HH}$=5.0 Hz, $^{3}J_{HH}$=9.0 Hz, 1H, CH$_2$CHCH=CH$_2$); 1.77; (dd, $^{2}J_{HH}$=5.0 Hz, $^{3}J_{HH}$=7.7 Hz, 1H, CH$_2$CHCH=CH$_2$); 2.62; (q, $^{3}J_{HH}$=8.5 Hz, 1H, CH$_2$CHCH=CH$_2$); 3.82; (t, $^{3}J_{HH}$=4.6 Hz, CH$_2$OH); 4.14-4.29; (m, 3H, CH$_2$OCO); 4.38; (dt, $^{2}J_{HH}$=10.7 Hz, $^{3}J_{HH}$=4.8 Hz, 1H, CH$_2$OCO); 5.13-5.20; (m, 1H, CH$_2$=CH); 5.27-5.37; (m, 1H, CH$_2$=CH); 5.41-5.53; (m, 1H, CH$_2$=CH). $^{13}$C NMR (101 MHz, CDCl$_3$): δ=14.2 (CH$_3$); 20.8; (CH$_2$CHCH=CH$_2$); 31.8; (CH$_2$CHCH=CH$_2$); 35.7; (COCCO); 60.9; (CH$_2$OH); 61.6; (CH$_2$OCO); 67.1; (CH$_2$OCO); 119.0; (CH$_2$=CH); 132.7; (CH$_2$=CH); 167.4; (C=O); 169.9; (C=O).

Step 2: Synthesis of 1-(2-ethylcarbamoyloxyethoxycarbonyl)-1-ethoxy-carbonyl-2-vinylcyclopropane (VCP-1)

To a stirred solution of 1-(2-hydroxyethoxycarbonyl)-1-ethoxycarbonyl-2-vinylcyclopropane (VCP-OH, 10.0 g, 43.8 mmol) and ethyl isocyanate (3.42 g, 48.2 mmol) in anhydrous methylene chloride (60.0 ml), a solution of dibutyltin dilaurate (138 mg, 0.22 mmol) in anhydrous methylene chloride (10 ml) was added under argon. Stirring continued for 3 h at RT. The solvent was distilled off under vacuum and ethyl acetate (150 ml) was added to the residue. The solution was washed with 5% NaOH (2×50 ml). The organic phase was dried over anhydrous sodium sulfate. The solvent was distilled off under vacuum. 11.95 g (91% yield) of a colourless liquid was obtained.

$^{1}$H NMR (400 MHz, CDCl$_3$): δ=1.14; (t, $^{3}J_{HH}$=7.2 Hz, 3H, NHCH$_2$CH$_3$); 1.26; (t, $^{3}J_{HH}$=7.2 Hz, 3H, OCH$_2$CH$_3$); 1.59; (dd, $^{2}J_{HH}$=4.8 Hz, $^{3}J_{HH}$=9.0 Hz, 1H, CH$_2$CHCH=CH$_2$); 1.73; (dd, $^{2}J_{HH}$=4.8 Hz, $^{3}J_{HH}$=7.6 Hz, 1H, CH$_2$CHCH=CH$_2$); 2.60; (q, $^{3}J_{HH}$=8.3 Hz, 1H, CH$_2$CHCH=CH$_2$); 3.12-3.30; (m, 2H, CH$_2$NH); 4.08-4.44; (m, 6H, CH$_2$OCO); 4.69; (s, 1H, NH); 5.11-5.17; (m, 1H, CH$_2$=CH); 5.26-5.34; (m, 1H, CH$_2$=CH); 5.39-5.51; (m, 1H, CH$_2$=CH). $^{13}$C NMR (101 MHz, CDCl$_3$): δ=14.2; (CH$_3$); 15.2; (CH$_3$); 20.5; (CH$_2$CHCH=CH$_2$); 31.4; (CH$_2$CHCH=CH$_2$); 35.8; (COCCO); 35.9; (CH$_2$NH); 61.5; (CH$_2$OCO); 62.2; (CH$_2$OCO); 63.7; (CH$_2$OCO); 118.7; (CH$_2$=CH); 132.9; (CH$_2$=CH); 155.9; (C=O); 167.1; (C=O); 169.4; (C=O).

Example 2

Synthesis of a TCD-diisocyanate-di-VCP-OH Adduct (VCP-2)

To a stirred solution of VCP-OH (9.14 g, 40.0 mmol) and dibutyltin dilaurate (166 mg, 0.26 mmol) in anhydrous methylene chloride (70.0 ml), bis(isocyanato-methyl)tricyclo[5.2.1.02'6]decane (TCD-diisocyanate (Lanxess), 5.13 g, 20.8 mmol) was added under argon. Stirring continued for 4 h at RT. The solution was washed with water (75 ml). The organic phase was dried over anhydrous sodium sulfate. The solvent was distilled off under vacuum and the crude product was purified by chromatography (flash silica gel with ethyl acetate/hexane: 1/1). 11.72 g (83% yield) of a colourless resin was obtained.

$^{1}$H NMR (400 MHz, CDCl$_3$): δ=0.80-2.55; (m, 24H, CH, CH$_2$, CH$_2$CHCH=CH$_2$, OCH$_2$CH$_3$); 2.60; (q, $^{3}J_{HH}$=8.3 Hz,

2H, CH$_2$CHCH=CH$_2$); 2.88-3.14; (m, 4H, CH$_2$NH); 4.13-4.45; (m, 12H, CH$_2$OCO); 4.67-4.90; (m, 2H, NH); 5.11-5.19; (m, 2H, CH$_2$=CH); 5.26-5.35; (m, 2H, CH$_2$=CH); 5.38-5.51; (m, 2H, CH$_2$=CH).

Example 3 (Comparison Example)

Synthesis of 1,8-bis(2-vinylcyclopropane-1-carboxylic Acid Ethyl ester-1-carbonyloxy)-3,6-dioxaoctane (VCP 5)

To a stirred solution of 1-ethoxycarbonyl-2-vinylcyclopropanecarboxylic acid (12.9 g, 69.9 mmol), triethylene glycol (5.0 g, 33.3 mmol) and DMAP (81 mg, 0.67 mmol) in anhydrous methylene chloride (40.0 ml), DCC (14.4 g, 69.9 mmol) was added portionwise under argon and at 0° C. Stirring continued for 30 min at 0° C. and 15 h at RT. The reaction mixture was suctioned over a frit and the residue was washed with methylene chloride (3×20 ml). The organic phase was washed with HCl 1N (75 ml), a saturated NaHCO$_3$ solution (75 ml) and a saturated NaCl (75 ml) solution. The organic phase was dried over anhydrous sodium sulfate. The solvent was distilled off under vacuum and the crude product was purified by chromatography (flash silica gel with ethyl acetate/heptane: 1/2). 11.6 g (72% yield) of a colourless liquid was obtained.

$^1$H NMR (400 MHz, CDCl$_3$): δ=1.26; (t, $^3J_{HH}$=7.2 Hz, 6H, OCH$_2$CH$_3$); 1.57; (dd, $^2J_{HH}$=4.9 Hz, $^3J_{HH}$=9.0 Hz, 2H, CH$_2$CHCH=CH$_2$); 1.71; (dd, $^2J_{HH}$=4.9 Hz, $^3J_{HH}$=7.6 Hz, 2H, CH$_2$CHCH=CH$_2$); 2.59; (q, $3J_{HH}$=8.4 Hz, 2H, CH$_2$CHCH=CH$_2$); 3.62; (s, 4H, OCH$_2$CH$_2$O); 3.69; (t, $^3J_{HH}$=4.9 Hz, 4H, OCH$_2$CH$_2$OCO); 4.12-4.35; (m, 8H, CH$_2$OCO); 5.10-5.16; (m, 2H, CH$_2$=CH); 5.25-5.33; (m, 2H, CH$_2$=CH); 5.37-5.49; (m, 2H, CH$_2$=CH). $^{13}$C NMR (101 MHz, CDCl$_3$): δ=14.2; (CH$_3$); 20.6; ( CH$_2$CHCH=CH$_2$); 31.4; (CH$_2$CHCH=CH$_2$); 35.8; (CO CCO); 61.5; (CH$_2$O); 64.6; (CH$_2$O); 68.9; (CH$_2$OCO); 70.6; (CH$_2$OCO); 118.6; (CH$_2$=CH); 133.0; (CH$_2$=CH); 167.2; (C=O); 169.6; (C=O).

Example 4

Determination of the Reactivity During Photopolymerization

The reactivity of the new monomers VCP 1 and VCP 2 was investigated in comparison with the reference compounds 1,1-bis(ethoxycarbonyl)-2-vinylcyclopropane (VCP 3) and bis-(2-vinyl-1,1-dicarboxylic acid monoethyl ester) resorcinyl ester (VCP 4) respectively. To each monomer, 0.5 mol.-% bis(4-methoxybenzoyl) diethyl germanium (Ivocerin®, Ivoclar Vivadent AG) was added as initiator and the mixture was polymerized in a Differential Scanning Calorimeter (Diamond model, Perkin Elmer) with a photopolymerization attachment by irradiation with an LED lamp (Bluephase model, Ivoclar Vivadent AG) for 2 minutes at 37° C. (I=20 mW/cm$^2$). The results are represented graphically in FIG. 1. The vinylcyclopropane according to the invention VCP 1 exhibits a considerably higher maximum of the polymerization rate in comparison with the reference compound VCP 3.

Figure 1:
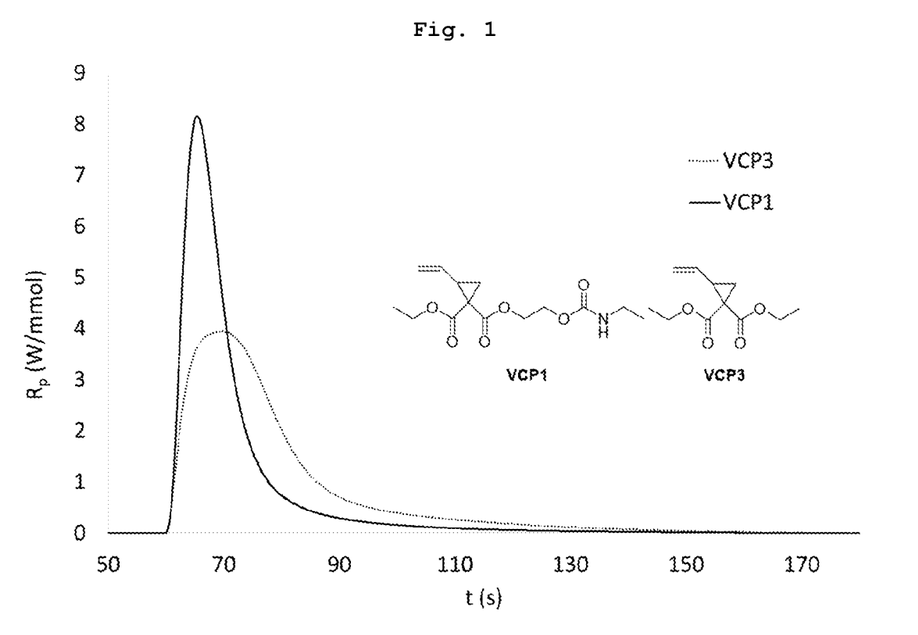
FIG. 1 shows graphical representations of the polymerization rate of a monomer according to the invention (VCP 1) and of a reference compound (VCP 3). The vinylcyclopropane according to the invention exhibits a considerably higher maximum of the polymerization rate in comparison with the reference compound. This shows that the compounds according to the invention polymerize more quickly than the comparison compounds.

The considerably higher maximum of the polymerization rate shows that the VCPs according to the invention polymerize, i.e. cure, considerably more quickly than the comparison compounds. The decisive disadvantage of the VCPs according to the state of the art is their slow polymerization.

Figure 2:
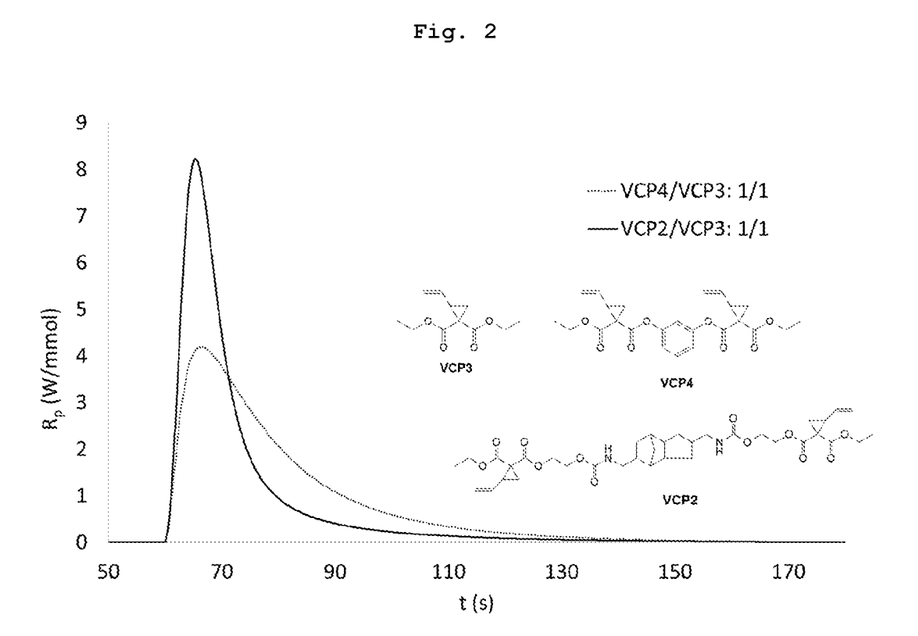
FIG. 2 shows graphical representations of the polymerization rate of a monomer mixture comprising a monomer according to the invention (VCP 2) and a reference compound (VCP 3) and of a mixture of two reference compounds (VCP 4/VCP 3) The mixture VCP 2/VCP 3 is considerably more reactive than the reference mixture VCP 4/VCP 3. The results show that the introduction of urethane groups results in a significant increase in the reactivity.

The reactivity of the mixtures VCP 2/VCP 3 (1 mol/1 mol) and VCP 4/VCP 3 (1 mol/1 mol) was then determined under the same conditions (0.5 mol.-% Ivocerin®, 37° C., I=20 mW/cm$^2$). It was established that the mixture VCP 2/VCP 3 is considerably more reactive than the reference mixture VCP 4/VCP 3 (FIG. 2). The results prove that the introduction of urethane groups leads to a significant increase in the reactivity.

Example 5

Preparation of Composites

Composites based on a mixture of VCP 2/VCP 5 (1/1: wt./wt.) and TCD 1/TEGDMA (1/1: wt./wt.) were prepared (Table 1). The composite pastes were prepared using kneaders. Corresponding test pieces were prepared from the materials which were irradiated 2 times for 3 mins with a dental light source (Spectramat®, Ivoclar Vivadent AG) and thus cured. The determination of the flexural strength and flexural modulus of elasticity was carried out in accordance with ISO standard ISO-4049 (Dentistry—Polymer-based filling, restorative and luting materials) (Table 2). The measurements were carried out after 24 h storage in water (37° C.). The shrinkage was determined by buoyancy (Archimedes method) (Table 2). The composite A based on the vinylcyclopropane according to formula I has a considerably lower polymerization shrinkage than the methacrylate-based composite B.

TABLE 1

Composition of the prepared composites

| Component | Composite A [wt.-%] | Composite B*[)] [wt.-%] |
|---|---|---|
| VCP 2 | 8.70 | — |
| VCP 5 | 8.70 | — |
| TCD 1[7)] | — | 8.70 |
| TEGDMA[1)] | — | 8.70 |
| Ivocerin ®[5)] (initiator) | 0.1 | 0.1 |
| EvoCeram ® isofiller SDI[6)] | 34.00 | 34.00 |
| Barium aluminium borosilicate glass filler[2)] | 33.50 | 33.50 |

TABLE 1-continued

Composition of the prepared composites

| Component | Composite A [wt.-%] | Composite B*[)] [wt.-%] |
|---|---|---|
| SiO$_2$—ZrO$_2$ Spherosil[3)] | 10.00 | 10.00 |
| YbF$_3$[4)] | 5.00 | 5.00 |

*[)]Comparative example
[1)]Triethylene glycol dimethacrylate
[2)]Glass powder GM 27884, 1 μm, silanized (Schott)
[3)]Tokoyama Soda,
[4)]Auer Remy
[5)]Bis(4-methoxybenzoyl) diethyl germanium
[6)]Composite filler: weight-average particle size 30-40 μm
[7)]

TCD 1

TABLE 2

Mechanical properties and volume shrinkage

| Composite | Flexural strength (MPa) | Flexural modulus of elasticity (GPa) | Volume shrinkage (vol.-%) |
|---|---|---|---|
| A | 128.3 ± 5.0 | 7.8 ± 0.4 | 2.7 ± 0.3 |
| B*[)] | 130.0 ± 8.9 | 10.2 ± 0.4 | 3.6 ± 0.5 |

*[)]Comparative example

Example 6

Preparation of Composites with Improved Mechanical Properties

Analogously to Example 5, the composite pastes based on VCP 4 were prepared (Table 3). VCP 1 and VCP 3 were used as diluents. The results of the mechanical properties are represented in Table 4 and show that the highly reactive vinylcyclopropane VCP 1 leads to an improvement in the mechanical properties in comparison with the vinylcyclopropane VCP 3 which corresponds to the state of the art.

TABLE 3

Composition of the composites

| Component | Composite D (wt.-%) | Composite E*[)] (wt.-%) |
|---|---|---|
| VCP 1 | 5.22 | — |
| VCP 3 | — | 5.22 |
| VCP 4 | 12.18 | 12.18 |
| Ivocerin ®[5)] | 0.1 | 0.1 |
| EvoCeram isofiller SDI[6)] | 34.00 | 34.00 |
| Barium aluminium borosilicate glass filler[2)] | 33.50 | 33.50 |
| SiO$_2$—ZrO$_2$ Spherosil[3)] | 10.00 | 10.00 |
| YbF$_3$[4)] | 5.00 | 5.00 |

*[)]Comparative example
[2-6)]as Table 1

TABLE 4

Mechanical properties of the composites

| Material | Flexural strength (MPa) | Flexural modulus of elasticity (GPa) |
|---|---|---|
| D | 108.8 ± 8.8 | 7.9 ± 0.4 |
| E*[)] | 83.3 ± 9.1 | 6.3 ± 0.6 |

*[)]Comparative example

The invention claimed is:

1. Dental material that comprises at least one vinylcyclopropane of general formula I in which the variables have the following meanings:
X, Y in each case are O or NH, wherein X and Y cannot have the same meaning,
$R^1$ is a branched or linear $C_1$-$C_4$alkyl radical,
$R^2$ is a linear or branched $C_2$-$C_4$ alkyl radical,
$R^3$ is an aliphatic linear or branched $C_1$-$C_{20}$-hydrocarbon radical, an aromatic $C_6$-$C_{14}$ radical, an aromatic or non-aromatic heterocyclic radical, which contains 4 to 12 carbon atoms and 1 to 2 heteroatoms, which are selected from N or O atoms, an alicyclic $C_6$-$C_{12}$-hydrocarbon radical, wherein in all cases the cyclic radicals can be mono- or polycyclic groups, or an aliphatic-aromatic $C_7$-$C_{20}$ radical, and
n is 1 or 2.

2. The dental material according to claim 1, which additionally comprises at least one further radically polymerizable monomer and an initiator for the radical polymerization.

3. The dental material according to claim 2, which comprises, as the further radically polymerizable monomer, at least one compound, which is selected from 1,1-di(ethoxycarbonyl)- or 1,1-di(methoxycarbonyl)-2-vinylcyclopropane, bis(2-vinylcyclopropane-1-carboxylic acid ethyl ester-1-carbonamido)-2,2-dimethyl-4-methylhexane, 1,8-bis(2-vinylcyclopropane-1-carboxylic acid ethyl ester-1-carbonyloxy)-3,6-dioxaoctane, the esters of 1-ethoxycarbonyl- or 1-methoxycarbonyl-2-vinylcyclopropanecarboxylic acid with ethylene glycol, 1,1,1-trimethylolpropane, 1,4-cyclohexanediol or resorcinol, bis-(2-vinyl-1,1-dicarboxylic acid monoethyl ester)resorcinyl ester, bicyclic cyclopropane derivatives, 2-(bicyclo[3.1.0]hex-1-yl)acrylic acid methyl or ethyl ester or the disubstitution products in 3-position thereof, (3,3-bis(ethoxy-carbonyl)-bicyclo-[3.1.0]-hex-1-yl)acrylic acid methyl or ethyl ester.

4. The dental material according to claim 2, which comprises, as the further radically polymerizable monomer, at least one mono- or polyfunctional (meth)acrylic acid derivative, which is selected from methyl, ethyl, 2-hydroxyethyl, butyl, benzyl, tetrahydrofurfuryl or isobornyl (meth)acrylate, p-cumylphenoxyethylene glycol methacrylate, bisphenol A di(meth)acrylate, an addition product of methacrylic acid and bisphenol A diglycidyl ether, ethoxylated or propoxylated bisphenol A dimethacrylate, bisphenol A dimethacrylate 2-[4-(3-methacryloyloxyethoxyethyl)phenyl]-2-[4-(3-methacryloyloxyethyl)phenyl]propane with 3 ethoxy groups, 2,2-bis[4-(2-(meth)acryloxypropoxy)phenyl]propane, an addition product of 2-hydroxyethyl methacrylate and 2,2,4-trimethylhexamethylene diisocyanate, an addition product of a mixture of 2-hydroxyethyl methacrylate and hydroxypropyl methacrylate with α,α,α',α'-tetramethyl-m-xylylene diisocyanate, di-, tri- or tetraethylene glycol di(meth)acrylate, trimethylolpropane tri(meth)acrylate, pentaerythritol tetra(meth)acrylate, glycerol di- and trimethacrylate, 1,4-butanediol di(meth)acrylate, 1,10-decanediol di(meth)acrylate, 1,12-dodecanediol di(meth)acrylate and acid-group-containing monomers.

5. The dental material according to claim 1, which additionally comprises at least one particulate filler.

6. The dental material according to claim 1, which additionally comprises at least one additive, which is selected from solvents, stabilizers, flavouring agents, dyes, microbiocidal active ingredients, fluoride-ion-releasing additives, optical brighteners, plasticizers and/or UV absorbers.

7. The dental material according to claim 1, which comprises
a) 2 to 95 wt.-% of at least one vinylcyclopropane of general formula I,
b) 0.01 to 5 wt.-% of at least one initiator for radical polymerization,
c) 0 to 80 wt.-% of other monomer(s), and optionally
d) 0 to 85 wt.-% filler(s),
in each case relative to the total mass of the material.

8. The dental material according to claim 7, which comprises 0 to 40 wt.-% filler(s), for use as coating material, or which comprises 10-70 wt.-% filler(s), for use as cement, or which comprises 10-85 wt.-% filler(s), for use as filling composite.

9. The dental material according to claim 8 for use as filling material, which comprises
a) 2 to 60 wt.-% of at least one vinylcyclopropane of general formula I,
b) 0.1 to 3 wt.-% of at least one initiator for the radical polymerization,
c) 0 to 50 wt.-% of other monomer(s), and
d) 10 to 85 wt.-% filler(s),
in each case relative to the total mass of the material.

10. A method of using a dental material which comprises at least one vinylcyclopropane according to claim 1 comprising manufacturing molded articles by a generative process.

11. The dental material according to claim 6,
wherein the solvents comprise water, ethanol or a mixture thereof and the stabilizers comprise polymerization stabilizers.

12. The dental material according to claim 1, which comprises
a) 2 to 90 wt.-% of at least one vinylcyclopropane of general formula I,
b) 0.1 to 3.0 wt.-% of at least one initiator for radical polymerization,
c) 0 to 60 wt.-% of other monomer(s), and optionally
d) 0 to 80 wt.-% filler(s),
in each case relative to the total mass of the material.

13. The dental material according to claim 1, which comprises
a) 10 to 85 wt.-% of at least one vinylcyclopropane of general formula I,
b) 0.2 to 2 wt.-% of at least one initiator for radical polymerization comprising a photoinitiator,
c) 0 to 50 wt.-% of other monomer(s), and optionally
d) 0 to 80 wt.-% filler(s),
in each case relative to the total mass of the material.

14. The dental material according to claim 8 for use as filling material, which comprises
a) 5 to 60 wt.-% of at least one vinylcyclopropane of general formula I,
b) 0.2 to 3.0 wt.-% of at least one initiator for the radical polymerization which comprises a photoinitiator,
c) 0 to 40 wt.-% of other monomer(s), and
d) 10 to 80 wt.-% filler(s),
in each case relative to the total mass of the material.

15. The dental material according to claim 8 for use as filling material, which comprises
a) 10 to 60 wt.-% of at least one vinylcyclopropane of general formula I,
b) 0.2 to 1 wt.-% of at least one initiator for the radical polymerization,
c) 0 to 30 wt.-% of other monomer(s), and
d) 10 to 80 wt.-% filler(s),
in each case relative to the total mass of the material.

* * * * *